United States Patent [19]

Adler-Moore et al.

[11] Patent Number: 5,043,107
[45] Date of Patent: Aug. 27, 1991

[54] PREPARATION SMALL UNILAMELLAR VESICLES INCLUDING POLYENE ANTIFUNGAL ANTIBIOTICS

[75] Inventors: Jill Adler-Moore; Ronald C. Gamble, both of Altadena; Richard T. Proffitt, Arcadia, all of Calif.

[73] Assignee: Vestar Research, Inc., Pasadena, Calif.

[21] Appl. No.: 427,732

[22] Filed: Oct. 27, 1989

Related U.S. Application Data

[60] Division of Ser. No. 259,356, Oct. 18, 1988, abandoned, which is a continuation of Ser. No. 899,064, Aug. 21, 1986, abandoned.

[51] Int. Cl.$^5$ .................. A61K 9/133; B01J 13/02
[52] U.S. Cl. ...................................... 264/4.6; 264/4.3; 424/450; 428/402.2; 436/829; 514/885
[58] Field of Search ............. 424/450; 436/829; 514/848

[56] References Cited

U.S. PATENT DOCUMENTS

| 4,394,149 | 7/1983 | Szoka, Jr. et al. ............... 424/60 X |
| 4,497,791 | 2/1985 | Gamble et al. ...................... 424/1.1 |
| 4,622,219 | 11/1986 | Haynes ............................... 424/450 |
| 4,663,167 | 5/1987 | Lopez-Berestein et al. ......... 514/37 |
| 4,766,046 | 8/1988 | Abra et al. .......................... 424/450 |

FOREIGN PATENT DOCUMENTS

| 0028917 | 5/1981 | European Pat. Off. . |
| 0119020 | 9/1984 | European Pat. Off. . |
| 0179444 | 4/1986 | European Pat. Off. . |
| 0272091 | 6/1988 | European Pat. Off. . |
| 0046921 | 3/1982 | Japan . |
| 8203769 | 11/1982 | PCT Int'l Appl. . |
| 8505030 | 11/1985 | PCT Int'l Appl. . |
| 8601103 | 2/1986 | PCT Int'l Appl. . |

OTHER PUBLICATIONS

Medoff, G and G. S. Kabayashi, N. Eng. J. Med., pp. 145-155 (1980).
Cohen, J. Lancet, 11, pp. 532-537 (1982).
Graybill, J. R. and P. C. Craven, Drugs, 25, pp. 41-62 (1983).
Mehta et al., Biochimica Et Biophysica Acta, 770, pp. 230-234 (1984).
Lopez-Berestein et al., J. Infect. Dis., 147, pp. 939-945 (1983).
Graybill et al., J. Infect. Dis., 145, pp. 748-752 (1982).
Adler Moore et al., Abst. for IXth Congress, Intern. Soc. for Human and Animal Mycology (1985).
Lopez-Berestein et al., Liposomal Amphotericin B for the Treatment of Systemic Fungal Infections in Patients with Cancer: A Preliminary Study, J. Inf. Dis., 151, pp. 704-710 (1985).
Juliano et al., Pharmokinetic and Therapeutic Consequences of Liposomal Drug Delivery: Fluorodeoxyuridino and Amphotericin B as Examples, Biologie Cellularaire, 47(1), pp. 39-46 (1983).
Mauk et al., Science, 207, pp. 309-311 (1980).
Mauk et al., Proc. Nat'l. Acad. Sci. (USA), 77, pp. 4430-4434, (1980).
Wu et al., Proc. Nat'l Acad. Sci. (USA), 78 pp. 2033-2037 (1981).
Jurgens, R. W. et al., Compatibility of Amphotericin B with Certain Large Volume Parenterals, Am. J. Hosp. Pharm., 38, pp. 377-378 (1981).
New, Antileishmanial Activity of Amphotericin and Other Antifungal Agents Encapsulated in Liposomes, 1981, 371-381 Journal of Antimicrobial Chemotherapy.
Tremblay, Efficacy of Liposome Intercalated Amphotericin B in the Treatment of Systemic Candidiasis Mice, 1984 170-173, Antimicrobial Agents & Chemotherapy.

Primary Examiner—Richard D. Lovering
Attorney, Agent, or Firm—Lyon & Lyon

[57] ABSTRACT

Formulations consisting of phospholipid small unilamellar particles encapsulating polyene antifungal antibiotics and methods for using such compositions to treat systemic fungal infections are described. In a preferred embodiment, the particles are in the form of vesicles which comprise a polyene antifungal antibiotic, preferably amphotericin B and/or nystatin, egg phosphatidylcholine and cholesterol, preferably in the molar ratio of about 0.2 (AMB):2(PL):1(CHOL). These vesicles may also have an amine modified surface. The vesicles are suspended in a low ionic strength saccharide/tris solution at a pH of from about 6.0 to about 8.0 and may be administered to deliver the anti-fungal antibiotic to treat systemic fungal infections.

11 Claims, No Drawings

PREPARATION SMALL UNILAMELLAR VESICLES INCLUDING POLYENE ANTIFUNGAL ANTIBIOTICS

This is a divisional of co-pending application Ser. No. 259,356 filed on Oct. 18, 1988, and now abandoned, which was a continuation of application Ser. No. 899,064 filed on Aug. 21, 1986 and now abandoned.

1. FIELD OF THE INVENTION

This invention relates to improved compositions consisting of phospholipid encapsulated polyene antifungal antibiotics. In another aspect it relates to the use of such compositions for the treatment of systemic fungal infections.

2. BACKGROUND

Systemic fungal infections occur most often in individuals with compromised immune systems. The causative agents of such infections are often fungi normally found in the human body or in the environment, but which are rendered noninvasive by a competent immune system. Such fungi are included in the genera Candida, Aspergillus, Cryptococcus, Histoplasma and Coccidioides. The patients most susceptible to these types of infections include those individuals with cancer, diabetes, alcoholism, drug addiction, extensive burns, organ transplants, immune deficiency diseases, and pregnancy. When these patients are on either chemotherapeutic, immunosuppressive and/or anti-bacterial regimens, the likelihood of contracting fungal infections is further increased. See Rippon, in Medical Mycology: The Pathogenic Fungi and the Pathogenic Actinomycetes, Saunders, (1979).

Treatment of systemic fungal infections is primarily limited to two groups of drugs: the polyene antibiotics such as amphotericin B and nystatin, and the imidazoles, such as ketaconazole and miconazole. Structurally, the polyene antibiotics contain three to seven conjugated double bonds. The double bonds are incorporated into a large ring (26 to 44 carbon atoms) lactone. On the opposite side of the macrocycle from the double bonds, the ring is substituted with from 6 to 12 hydroxyl groups mainly in 1,3 relationships but also in 1,2 and 1,4 relationships. Amphotericin B and nystatin possess both an attached aminosugar and a carboxylic acid group. The opposing effects of the lipophilic polyene region and the lipophobic polyol region render polyenes poorly soluble in water.

The preferred treatment of systemic fungal infections is the administration of amphotericin B (Fungizone) because it is the most effective systemic antifungal drug and is associated with the least number of reoccurrences. The polyenes are not absorbed from the gastrointestinal tract following oral administration and have to be administered by I.V. infusion. Amphotericin B and nystatin however both exhibit acute and chronic toxicity to the cells of the patient and thus the doses which may be administered are limited, often preventing complete cure. In fact, nystatin has only been available for inhalation therapy, and oral and topical use for this reason.

The polyene antifungal antibiotics bind readily to sterols present in cell membranes of animal cells, for example cholesterol, and cause disruption of membrane permeability and cell lysis. The toxicity of amphotericin-B in mammals has been found to be greater for certain membrane systems, such as the renal tubules. Clinical use of amphotericin-B has been associated with acute hemolytic crisis and eventual kidney failure at therapeutic dose levels. Medoff, G. and G.S. Kabavashi, N. Eng. J. Med., 303, p. 145–155 (1980); Cohen, J., Lancet 11, p. 532–537 (1982); Graybill, J.R. and P.C. Craven, Drugs, 25, p. 41–62 (1983).

Studies in animals models, and to a limited extent in humans, have shown that amphotericin B incorporated into phospholipid vesicles (liposomes) exhibits decreased host toxicity when used to treat systemic fungal infections. It is expected, based on the fact that nystatin has the same mechanism of action as amphotericin B, that nystatin incorporated into phospholipid vesicles also exhibits decreased host toxicity. Free and liposomal Amphotericin B are approximately equipotent in treating disseminated Candidiasis in mice. (Mehta et al. Biochimica et Biophysica Acta, 770, p. 230–234 (1984)). Therefore, drug doses of liposomal amphotericin B which exceed the maximum tolerated dose for free amphotericin B can be administered which results in a marked improvement in the survival of infected mice. Id. For example, liposome encapsulated amphotericin-B has been used to treat murine systemic fungal infections such as Candidiasis, (Lopez-Berestein et al., J. Infect. Dis. 147, p. 939–945 (1983)), Cryptococcosis (Graybill et al., J. Infect. Dis., 145, p. 748–752 (1982)), and Histoplasmosis (Taylor et al., Am. Rev. Respir. Dis., 125, p. 610–611 (1982); Adler-Moore et al., Abst. for IXth Congress, Intern. Soc. for Human and Animal Mycol., (1985)), and to treat terminally ill human cancer patients that have not responded to traditional amphotericin-B therapy (Lopez-Berestein et al., Abst. for 23rd. Intersci. Conf. on Antimicrob. Agents and Chemotherapy (1983); Lopez-Berestein et al., Liposomal Amphotericin B for the Treatment of Systemic Fungal Infections in Patients with Cancer: A Preliminary Study, J. Inf. Dis., 151, 704–710 (1985)). Using this type of liposomal drug delivery, the amount of polyene antifungal antibiotic that can be safely administered and the therapeutic index of the drug can be significantly increased.

In most of the studies referenced above, multilamellar vesicles (MLVs) have been used. The size of these vesicles (0.2–5 $\mu$) favors the phagocytosis of the drug-containing vesicles by macrophages. When introduced into the bloodstream, fungi are also initially phagocytized by macrophages in the organs of the reticuloendothelial system (RES) such as the liver, lung and spleen. When the fungi invade other tissues, macrophages which are an important part of the immune response to fungal infections, migrate to these sites and become associated with infected sites. Because of the multilamellar composition of the MLVs, encapsulation of a large amount of amphotericin B can be readily achieved. A greater than 90% encapsulation efficiency for MLVs has been reported. Juliano et al., Pharmokinetic and therapeutic consequences of liposomal drug delivery: Fluoro deoxuridine and Amphotericin B as examples, Biology of the Cell, 97, 39–46 (1983). Unfortunately, MLVs are generated as populations of vesicles which are heterogeneous in size, and this makes it very difficult to standardize preparations manufactured in different batches. Such vesicles may be undesirable to administer into mammals because the larger particle sizes (often several microns), and their likely aggregation and fusion to form even larger particles during storage, enhances the possibility of embolism to organs, particularly the lungs, following administration. Taylor et al., Am. Rev. Respir. Dis., 125, p. 610-611 (1982). Finally, unlike small unilamellar particles, MLVs are difficult to sterilize by filtration.

Recently, amphotericin-B has been encapsulated in small unilamellar vesicles (SUVs) (less than 1 micron) as described by Tremblay et al., *Antimicrob. Agents Chemother.*, 26, p. 170-173 (1984) and suspended in saline solution. Higher host survival rates and lower viable colony counts of fungi from the kidneys, liver and spleen as compared with those for unencapsulated drug were observed in mice with disseminated Candidiasis treated with SUV encapsulated amphotericin B. The acute 50% lethal dose ($LD_{50}$), a standard measure of acute toxicity, was 11.8 mg/kg as compared to 2.3 mg/kg for unencapsulated drug. Only a 70% encapsulation efficiency was achieved with these SUVs.

The formulations utilized in the Tremblay et al. study also did not include modification of the vesicles to induce preferential uptake by the RES, and as such only a fraction of the SUVs are likely to be taken up by organs containing macrophages. In investigations using egg phosphatidylcholinecholesterol vesicle formulations, similar to those of Tremblay et al., supra, only 40 to 60% of the administered radiolabel used to label the vesicles became associated with major organs of the RES. In earlier work, vesicle formulations with aminosugar derivatives on their surfaces have been shown to induce chemotaxis and subsequent uptake by polymorphonuclear leukocytes when injected subcutaneously into mice. Mauk et al., *Science*, 207, p. 309-311 (1980); Mauk et al., *Proc. Nat'l. Acad. Sci.* (USA), 77, p. 4430-4434 (1980). When SUVs having the 6-aminomannose derivative of cholesterol associated with the membrane are injected intravenously, three-fourths of the radiolabeled vesicles are in the liver and spleen within three hours. Id. Later work by Wu and colleagues confirmed that incorporating an extended amine on a micelle's surface enhances phagocytosis by mouse peritoneal macrophages. Wu et al., *Proc. Nat'l Acad. Sci.* (USA), 78, p. 2033-2037 (1981). SUVs having an amine modified surface have also been used to label phagocytic cells in vitro, such as leukocytes, to detect sites of infections. U.S. Pat. No. 4,497,791. Until the present invention, however, in situ targeting of SUVs for macrophages of the RES to assist in treating fungal infections has not been achieved.

It is an object of the present invention to provide stable, homogeneous liposomes (SUVs) with encapsulated polyene antifungal antibiotics in commercial quantities, which would remain intact in the bloodstream until entering the macrophage-containing organs of the RES, such as the liver and the spleen. Another object of this invention is to target the SUVs encapsulating amphotericin B to the macrophages which carry the drug directly to sites of fungal infection. This method of delivery could enhance the therapeutic index of the SUV encapsulated drug over unencapsulated drug and lower the acute and chronic toxicity of the drug. Still another object of the invention is to provide a method for using these improved formulations of encapsulated polyene antifungal antibiotics to treat systemic fungal infections.

3. SUMMARY OF THE INVENTION

Injectable compositions comprising polyene antifungal agents encapsulated in liposomes consisting of phospholipids and cholesterol which may also have an amine modified surface are described. The liposomes are suspended in a low ionic strength aqueous phase such as a saccharide solution. The pH of this aqueous phase is preferably between about 6.0 to 8.0. These compositions are administered intravenously to treat systemic fungal infections.

4. DETAILED DESCRIPTION OF THE INVENTION

Anti-fungal preparations are obtained using specific formulations in the form of small unilamellar vesicles to encapsulate polyene antifungal antibiotics such as amphotericin B and nystatin and suspending said particles in a low ionic strength aqueous phase in which a mono- or disaccharide is dissolved. This aqueous phase is physiologically isotonic having a pH of about 6.0 to 8.0. These preparations may be further improved by the modification of the surface of the vesicles with an amine for example, to provide for recognition by macrophages of the mammalian body which allows for targeting to the RES and thus enhanced effectiveness of anti-fungal therapy.

Methods for forming small vesicles are well known and include methods which provide sufficient shear force (e.g. sonication, homogenization, detergent dialysis, etc.). We have found that small vesicles useful in the present invention may be obtained by sonicating or homogenizing the following components: polyene antifungal antibiotic, at least one phospholipid, cholesterol, and optionally 6-aminomannose derivatives of cholesterol.

The preferred composition for use in this invention consists of a polyene antifungal antibiotic, at least one phospholipid, and cholesterol in a low inonic strength aqueous phase of about pH 6.0 to 8.0 in the molar ratio AMB:PL:CHOL 0.2:2:1.

Any number of well-known phospholipids may be used singly or in combination to form the vesicles. Representative of such phospholipids are: phosphatidylcholine (hereinafter referred to as "PC"), both naturally occurring and synthetically prepared, phosphatidic acid (hereinafter referred to as "PA"), phosphatidylserine (hereinafter referred to as "PS"), phosphatidylethanolamine (hereinafter referred to as "PE"), phosphatidylglycerol (hereinafter referred to as "PG"). The PC, PG, PA and PE may be derived from purified egg yolk. Saturated synthetic PC and PG, such as dipalmitoyl may also be used.

Cholesterol may be present in a range of 0.10-40 mole %. If too much cholesterol is used, it may interfere with the polyene antifungal antiobiotic binding to sterols such as ergosterol in the fungal membranes. However, cholesterol imparts stability to the vesicle and thus a certain amount is desirable to prevent leakage of the highly toxic drug. It is preferred that a concentration of at least 1 mg polyene antifungal antibiotic/ml is obtained for injection.

The use of a low ionic strength aqueous phase to suspend the vesicles improves vesicle stability. The low ionic strength aqueous phase is composed of mono- or disaccharides dissolved in Tris buffer. When using a monosaccharide such as glucose, fructose, or galactose, a 4-6% solution is desired; an 8-10% solution is desired when a disaccharide such as sucrose or lactose is used. Unlike the prior art processes which used saline as the suspending solution which causes precipitation of non-liposomal amphotericin B (Jurgens, R. W. et al. Compatibility of Amphotericin B with certain large-volume parenterals, *Am. J. Hosp. Pharm.* 1981, 38, 377-78), the use of saccharide in the low ionic strength aqueous phase is not associated with polyene antifungal antibiotic precipitation, thus increasing the liposome encapsulation efficiency and stability.

Targeting of the vesicles of this invention to the macrophages in the RES system may also be preferably achieved using an extended amine molecule incorporated into the surface of the vesicles using the methods described herein. In a preferred embodiment the amine is a 6-aminomannose derivative of cholesterol.

The first step in the process of the invention is to mix at least one phospholipid and cholesterol dissolved in an organic solvent such as a four to eight carbon aliphatic alcohol, e.gs., octanol and heptanol, with a DMSO (dimethylsulfoxide) or dimethylformamide solution of the polyene antifungal antibiotic.

Upon evaporation of the solvent, the phospholipid along with the lipid cholesterol and polyene antifungal antibiotic remain on the sides of a suitable reaction vessel.

An aqueous phase of low ionic strength (less than 20 mM) and pH 6.0-8.0 comprised of a mono- or disaccharide dissolved in Tris buffer is then added to the vessel. The lipid component and polyene antifungal antibiotic, previously deposited on the vessel walls are hydrated and suspended with mixing. The mixture as obtained above is sonicated with the use of a micro-probe sonicator (Sonics & Materials, Inc., Model VC800) for about 12-45 minutes. The preparation is then subjected to centrifugation to remove larger particles and leave a suspension of small, unilamellar vesicles. The vesicles may be sterilized by passage through a $0.8\mu$ and then a $0.45\mu$ filter.

This filtered preparation of small, unilamellar vesicles can then be lyophillized to a thin film or powder which is stable and can be stored for future use. Lyophilization refers to the process whereby a substance is prepared in dry form by rapid freezing and dehydration under high vacuum. The vesicle-encapsulated polyene antifungal antibiotic is made ready for use as an injectable composition against fungal infections by the addition of sterile, distilled water to this powder and incubation at 37° C. for about 15 minutes with occasional shaking.

The amount of polyene antifungal antibiotic encapsulated in the resulting vesicles prepared according to the methods described herein, may be determined using, for example, a high-pressure liquid chromatography (HPLC) assay, or a spectrophotometric assay using the extinction coefficient of the antibiotic at the wavelength of maximum absorption. The size of the resulting vesicles may be determined using light scattering procedures. The vesicles prepared by the procedures described herein have been found to be stable upon storage.

To determine the usefulness of the vesicle formulations of this invention, the preparations of encapsulated polyene antifungal antibiotics are administered into animal models, such as mice and various parameters are examined. To demonstrate toxicity and biological effectiveness of the vesicles of this invention, both acute and chronic toxicity are assessed. For acute toxicity, various amounts of SUV encapsulated polyene antifungal antibiotic may be injected intravenously into mice. Controls are used to determine the $LD_{50}$ for unencapsulated drug. Chronic toxicity in humans is reflected in liver and kidney function. Such toxicity may be indicated in a dog model by testing sera for transaminase activity (SGOT/SGPT), blood urea nitrogen (BUN), and creatinine levels. Dogs are injected with subacutely toxic (therapeutic) levels of encapsulated or unencapsulated drug for several days. Blood samples are taken from survivors over specified time periods and tested and compared to control sera obtained from healthy dogs.

The efficacy of anti-fungal therapy using encapsulated and unencapsulated polyene antifungal antibiotics may be compared also using an animal model. Mice may be inoculated using a lethal or sublethal dose of a virulent strain of fungus, such as Candida albicans. The mice are then examined for mortality (lethal dose) or sacrificed at a specified time after injection (sublethal dose) and the fungal colony-forming units from extracts of the kidneys determined. The development of fungal colonies from the kidney extracts indicates whether the fungal infection has completely resolved.

The stability of the vesicles in the bloodstream and uptake by various tissues in the body such as the RES are also determined to demonstrate the utility of the preparations of the present invention.

The examples which follow illustrate the preparation, characterization and in vivo application in an animal model of encapsulated amphotericin B using the vehicle formulations of the present invention.

The following examples are presented solely to illustrate the invention, and are not intended to be limiting in any way.

PREPARATION OF VESICLE ENCAPSULATED AMPHOTERICIN B

Examples A-C

A stock solution of amphotericin B (Squibb) was prepared using 25 mg amphotericin B per ml DMSO. The solution was shaken well until all the amphotericin B dissolved. Egg phosphatidylcholine (Avanti) was prepared using 27 mg of lecithin per ml of octanol. This solution was stored at room temperature until use. An 8 mg/ml octanol solution of cholesterol (Calbiochem) was prepared and also stored at room temperature. Aminomannose obtained from Vestar Research Inc. (Pasadena, CA) was prepared using 3 mg of aminomannose per ml of chloroform and stored in the freezer. Using 250 ml round bottom flasks, phospholipid vesicles were prepared by mixing stock solutions of amphotericin B (AMB), egg phosphatidylcholine (PL), cholesterol (CHOL), and aminomannose in various molar ratios as set forth in Table 1. The organic solvents were evaporated using a rotavaporator and a very strong vacuum for 1 to 1 ½ hours at 65° C. The resulting film was placed under vacuum on a lyophilizer overnight. This film may be stored for up to one week on the lyophilizer before the vesicles are made.

To the film described above, 8 ml phosphate buffered saline (PBS) [pH 7.2] was added to each 250 ml round bottom flask, and stirred at low temperatures with a small magnetic stirrer. Two ml more of PBS were added to each flask for rinsing. Multiple 2 ml aliquots of the suspension containing multilamellar vesicles (MLVs) were sonicated for 15 minutes in a water bath sonicator (Sonics & Material, Inc.) in a glass, roundbottomed screw cap culture tube. The resulting solution containing SUVs was centrifuged at 2500 rpm for 10 minutes to remove insoluble materials and the supernate from this centrifugation was run through a Sephadex 50-80 column in PBS [pH 7.2]. The column was prepared in a 5 ml syringe, and after the SUVs were loaded onto it, it was centrifuged at 2500 rpm for 10 minutes to remove unincorporated amphotericin B and any other insoluble materials. The resulting SUV suspension covered with foil was stored at room temperature. Upon subsequent use, the preparations were heated to 37° C. for 15 minutes and then centrifuged at 2500 rpm for 10 minutes to remove any insoluble material that may have formed on storage.

EXAMPLES D-O

A stock solution of amphotericin B (Squibb) was prepared using 25 mg amphotericin B per ml DMSO and shaken well until all the amphotericin B had dissolved. Egg phosphatidylcholine (PL) (Avanti) was prepared using 20 mg of lecithin per ml of octanol. This solution was stored at room temperature until use. A 20 mg/ml octanol solution of cholesterol (Calbiochem) was prepared and also stored at room temperature. The stock solution of aminomannose contained 3 mg/ml chloroform solution of aminomannose (Vestar Research, Inc., Pasadena, CA). Phospholipid vesicles were prepared by mixing stock solutions of amphotericin B (AMB), egg phosphatidylcholine (PL), cholesterol (CHOL), and aminomannose (AM) in various molar ratios as set forth in Table 1 in 125 ml round bottom flasks.

The organic solvents were evaporated using a rotavaporator and a very strong vacuum for about 45-60 minutes at 65° C. The resulting film was placed under a vacuum on a lyophilizer overnight, and stored under nitrogen in the freezer for up to 2 weeks. The flask was kept covered with foil.

To the film obtained as described above 10 ml of 5% dextrose in 10 mM Tris-Cl (pH 7.2) was added to each flask and each flask heated in a 65° C. water bath for 40 minutes. The film in the flask was resuspended by vigorous shaking and then by using a small magnetic stirrer to remove those parts of the film that were difficult to resuspend. The suspension containing multilamellar vesicles (MLVs) was sonicated for at least 12 minutes at 65° C. with a probe sonicator (Sonics and Materials, Inc., Model VC800) in a glass conical flask. The resulting preparation containing SUVs was centrifuged at 2500 rpm for 10 minutes to remove insoluble materials and it was then filtered through a $0.8\mu$ and then a $0.45\mu$ filter.

For Examples E and H only, 8 ml of the filtered preparation obtained above was transferred to a round bottom flask and frozen as a thin film in a dry ice/isopropanol bath. This flask was placed on the lyophilizer for 4 days. At that time, the flask was removed from the lyophilizer and 8 ml sterile distilled water was added to the film. Thereafter, the flask was incubated at 37° C. for 15 minutes with intermittent shaking to resuspend the lyophilized film preparation.

For Example H only, soy phosphatidylcholine (PL) was substituted for egg phosphatidylcholine.

CHARACTERIZATION OF ENCAPSULATED AMPHOTERICIN B VESICLES

The amount of amphotericin B associated with each of the SUV suspensions using the procedures set forth above is shown in Table 1 as determined by HPLC analysis and by spectrophotometric analysis using the extinction coefficient of amphotericin B at 406 $\lambda$.

The size of the SUVs prepared according to the present invention is determined by heating the SUV suspension to 65° C. for 10 minutes and placing a 0.025 ml sample into a Nicomp Model 200 Laser Particle Analyzer. Using a Gaussian distribution curve, the mean diameter and standard deviations of the SUVs are also shown in Table 1.

ANIMAL STUDIES

Mice infected with *Candida albicans* were intravenously inoculated five hours after infection with encapsulated amphotericin B or unencapsulated amphotericin B (Fungizone) using a single dose. At 21 days post-infection, the surviving animals were sacrificed and their kidneys cultured for Candida. Twenty-one day survival was used to determine the dose that protected 50% of the animals from death ($PD_{50}$) and the kidney culture test was used to determine the dose that cured 50% of the surviving animals ($ED_{50}$). The results are set forth in Table 1.

To determine chronic toxicity, amphotericin B liposomes prepared by Vestar Research, Inc., as an aqueous formulation containing 1.737 mg of amphotericin B/ml, were administered intravenously to four dogs, once daily for 4 days, at a daily dose of 5 mg of amphotericin B/kg. Injections were given at a rate of 0.5 ml/sec. Blood samples for determination of serum urea nitrogen, creatinine, GPT, and alkaline phosphatase were taken prior to the first dose and on the morning after the last dose. Results are presented in Table II. For comparison, Table III presents results from a dog study using unencapsulated amphotericin B (Fungizone) on a different dose schedule.

RESULTS

The dose needed to produce acute intravenous toxicity ($LD_{50}$) in an animal model was increased to a level greater than 21.2 mg amphotericin B/kg which is approximately 10 times more than unencapsulated drug and approximately two times more than the Tremblay formulation. Furthermore, over 90% of the amphotericin B is encapsulated in the present invention, an encapsulation efficiency heretofore only observed with MLVs. The preparation is at least as efficacious as unencapsulated amphotericin B as measured by animal survival and viable colony counts in certain organs in animals infected with the fungi.

It appears from the chronic toxicity study in dogs that the encapsulated form of this invention is approximately 1.5 to 2 times less toxic than unencapsulated amphotericin B. (See tables II and III).

Clinical observations included inactivity and depression in all dogs throughout the study following administration of the daily dose. One dog became extremely lethargic and experienced body tremors on day 4. Mild to moderate injection of the sclera of both eyes occurred in all animals during on shortly after dosing. Lacrimation was observed in three dogs following the first dose and was accompanied by slight salivation and a nasal discharge in one dog. Other symptoms noted after dosing were retching, emesis, emesis with blood, soft and loose feces with blood, and/or dark tarry feces. At the end of the dosing period, serum urea nitrogen was markedly elevated, and serum creatinine, GPT, and alkaline phosphatase were moderately elevated. Two of the dogs were sacrificed in poor condition on the day after the last dose.

Although this specification has been disclosed and illustrated with reference to particular applications, the principles involved are susceptible to numerous other applications which will be apparent to persons skilled in the art. The invention, therefore, is to be limited only as indicated by the scope of the appended claims.

TABLE I

| EXAMPLE | MOLAR RATIO (AMB:PL:CHOL:AM) | PREPARATION | AMT AMB (mg/ml) | SIZE | $LD_{50}$ (mg/kg) | $PD_{50}$ (mg/kg) | $ED_{50}$ (mg/kg) |
|---|---|---|---|---|---|---|---|
| N | .2:2:1:0 | Sonicated 36 minutes | 1.60 | 126.7 (38.3) | 15.0; 17.8**** | | |
| O | .2:2:1:0 | Sonicated 20 minutes | 1.50 | 101.1 (30.4) | 20; 30**** | | |
| Fungizone | | | | Approx. 2-3 | | .20 | .30 |

Abbreviations:
AMB = Amphotericin B
PL = Egg Phosphatidylcholine (phospholipid)
CHOL = Cholesterol
AM = 6-Aminomannose
LD50 = Acute toxicity
PD50 = 21-day Survival
ED50 = Kidney Clearance
NOTES:
*Example H - Soybean phosphatidylcholine substituted for egg phosphatidylcholine
**11-day survival; holiday interference
***4 days later, sample stored in refrigerator
****$LD_{50}$ of sample determined at weekly intervals

TABLE II

Amphotericin B Liposomes: Four-Day Intravenous Screening Study in Dogs$^a$

| Dog No. and Sex | Serum Urea Nitrogen (mg/dl) | | Serum Creatinine (mg/dl) | | Serum Gpt (IU/L) | | Serum Alkaline phosphatase (IU/L) | |
|---|---|---|---|---|---|---|---|---|
| | Pre-test | Day 5 | Pre-test | Day 5 | Pre-test | Day 5 | Pre-test | Day 5 |
| 5199 M | 12 | 86 | 0.9 | 2.4 | 20 | 76 | 62 | 92 |
| 5235 M | 12 | 243 | 0.8 | 6.6 | 26 | 121 | 76 | 286 |
| 5160 F | 11 | 169 | 0.8 | 4.8 | 23 | 163 | 63 | 164 |
| 5162 F | 12 | 96 | 0.7 | 2.9 | 22 | 99 | 53 | 128 |
| Normal Range | 9-24 | | 0.7-1.0 | | 15-48 | | 29-114 | |

$^a$5 mg of amphotericin b/kg daily

TABLE III

Fungizone ® Intravenous: Two-Week Intravenous Screening Study in Dogs

| Daily Dose of Ampho. B | Dog No. and Sex | Serum Urea Nitrogen (mg/ml) | | Serum Creatinine (mg/dl) | | Serum GPT (IU/l) | | Serum Alkaline Phosphatase (B-L-B units) | |
|---|---|---|---|---|---|---|---|---|---|
| | | Pretest | Week 2 | Pretest | Week 2 | Pretest | Week 2 | Pretest | Week 2 |
| 2.5 mg/kg | 813 M | 12 | >196$^a$ | 1.1 | 7.0$^a$ | 29 | 185$^a$ | 1.1 | 4.9$^a$ |
| | 814 M | 19 | >93 | 1.2 | 5.4 | 22 | 44 | 0.5 | 2.9 |
| | 815 F | 14 | >93 | 0.9 | 4.6 | 18 | 23 | 1.9 | 3.2 |
| | 816 F | 13 | 152 | 0.9 | 4.5 | 29 | 48 | 1.2 | 2.2 |
| 1.25 mg/kg | 822 M | 16 | 80 | 0.9 | 2.2 | 21 | 20 | 1.4 | 1.7 |
| | 823 M | 12 | 79 | 0.7 | 2.3 | 20 | 19 | 2.2 | 2.8 |
| | 824 F | 16 | 86 | 0.9 | 3.2 | 23 | 27 | 1.2 | 2.0 |
| | 825 F | 16 | 82 | 0.5 | 3.2 | 20 | 28 | 1.4 | 2.4 |
| 0.625 mg/kg | 826 M | 17 | 28 | 0.9 | 1.2 | 30 | 33 | 2.0 | 2.1 |
| | 827 M | 22 | 49 | 1.1 | 1.6 | 26 | 25 | 2.3 | 3.1 |
| | 828 F | 17 | 37 | 0.8 | 1.2 | 19 | 29 | 1.9 | 2.4 |
| | 829 F | 14 | 34 | 0.6 | 1.1 | 20 | 20 | 2.6 | 2.9 |
| NORMAL RANGE | | 11-29 | | 0.6-1.3 | | 13-50 | | 0.5-3.5 | |

$^a$Day of necropsy.

We claim:

1. A process for preparing an injectable composition comprising small unilamellar vesicles including a polyene antifungal antibiotic, comprising the steps of:
   a) dissolving at least one phospholipid and cholesterol in an aliphatic alcohol having from four to eight carbon atoms;
   b) dissolving a polyene antifungal antibiotic in a solvent selected from the group consisting of dimethylsulfoxide and dimethylformamide;
   c) mixing the solutions of steps (a) and (b);
   d) evaporating the mixed solvents to produce a lipid cholesterol antibiotic mixture;
   e) hydrating the mixture with an aqueous phase of low ionic strength; and
   f) forming small unilamellar vesicles containing the polyene antifungal antibiotic from the hydrated mixture.

2. The process of claim 1 in which the aliphatic alcohol is selected from the group consisting of heptanol and octanol.

3. The process of claim 1 or 2 in which the aqueous phase is a saccharide solution.

4. The process of claim 3 in which the polyene antifungal antibiotic, at least one phospholipid, and cholesterol are in a mole percentage ratio ranging from about 5-15 mole percent polyene antifungal antibiotic, about 40-90 mole percent phospholipid and about 10-40 mole percent cholesterol.

5. The process of claim 3 in which the polyene antifungal antibiotic is selected form the group consisting of amphotericin B and nystatin.

6. The process of claim 3 in which the saccharide is selected from the group consisting of sucrose, lactose, glucose, fructose and galactose.

7. The process of claim 6 in which the polyene antifungal antibiotic, at least one phospholipid, and cholesterol are in a mole percentage ratio ranging from about 5-15 mole percent polyene antifungal antibiotic, about 40-90 mole percent phospholipid and about 10-40 mole percent cholesterol.

8. The process of claim 6 in which the polyene antifungal antibiotic is selected from the group consisting of amphotericin B and nystatin.

9. The process of claim 1 or 2 in which the polyene antifungal antibiotic, at least one phospholipid, and cholesterol are in a mole percentage ratio ranging from about 5-15 mole percent polyene antifungal antibiotic, about 40-90 mole percent phospholipid and about 10-40 mole percent cholesterol.

10. The process of claim 9 in which the polyene antifungal antibiotic is selected from the group consisting of amphotericin B and nystatin.

11. The process of claim 1 or 2 in which the polyene antifungal antibiotic is selected from the group consisting of amphotericin B and nystatin.

* * * * *